US011420068B2

(12) United States Patent
Hsung et al.

(10) Patent No.: US 11,420,068 B2
(45) Date of Patent: Aug. 23, 2022

(54) METHOD AND MEDICAL DEVICE FOR IMPLEMENTING DUAL-CHAMBER PACING MODE WITHOUT VENTRICULAR PACING

(71) Applicant: MICROPORT SOARING CRM (SHANGHAI) CO., LTD., Shanghai (CN)

(72) Inventors: Jean Cheui Hsung, Shanghai (CN); Min Huang, Shanghai (CN); Guiling Li, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 23 days.

(21) Appl. No.: 16/959,092

(22) PCT Filed: Dec. 29, 2018

(86) PCT No.: PCT/CN2018/125799
§ 371 (c)(1),
(2) Date: Jun. 29, 2020

(87) PCT Pub. No.: WO2019/129301
PCT Pub. Date: Jul. 4, 2019

(65) Prior Publication Data
US 2020/0391034 A1    Dec. 17, 2020

(30) Foreign Application Priority Data
Dec. 29, 2017  (CN) .......................... 201711475110.3

(51) Int. Cl.
*A61N 1/36*  (2006.01)
*A61N 1/368*  (2006.01)
*A61N 1/02*  (2006.01)

(52) U.S. Cl.
CPC ........... *A61N 1/3684* (2013.01); *A61N 1/025* (2013.01); *A61N 1/3688* (2013.01)

(58) Field of Classification Search
CPC .... A61N 1/3684; A61N 1/025; A61N 1/3688; A61N 1/3627; A61N 1/365; A61N 1/368
See application file for complete search history.

(56) References Cited

U.S. PATENT DOCUMENTS 5,626,621 A    5/1997  Skoglund et al.
6,330,477 B1 * 12/2001  Casavant ........... A61N 1/39622
                                                        607/14
(Continued)

FOREIGN PATENT DOCUMENTS

CN    1897872 A    1/2007
CN    1942217 A    4/2007
(Continued)

OTHER PUBLICATIONS

Jiang et al., "Current research status of triple-site cardiac resynchronization therapy," Journal of Clinical Cardiology (China), 2015, vol. 6, pp. 586-590, 5 pages.

*Primary Examiner* — Rex R Holmes
(74) *Attorney, Agent, or Firm* — Muncy, Geissler, Olds & Lowe, P.C.

(57) ABSTRACT

A method and a medical device for implementing a dual-chamber pacing mode without ventricular pacing are disclosed. The method includes: obtaining pacing mode information configured by a user; controlling a dual-chamber pacemaker to operate in an ADD mode and detecting whether there is a need for delivering a pace; and performing a predetermined interruption process if a need for delivering a pace is detected. The predetermined interruption process includes: 2041) determining whether a chamber to be subsequently paced is a ventricle; 2042) if it is determined that the chamber to be subsequently paced is a ventricle, determining whether there is a need for delivering a real ventricular pace; 2043) if delivery of a real ventricular pace is not needed, delivering a virtual ventricular pace VVP and resetting a first atrial escape interval; and returning after the predetermined interruption process is terminated. According to the present method and device, physiological transitioning to or from a DDD mode is enabled when so desired, resulting in reduced patient discomfort. In addition, (Continued)

enhanced implementation convenience, reliability and direct validatability with reduced verification workload can be achieved.

8 Claims, 8 Drawing Sheets

(56) References Cited

U.S. PATENT DOCUMENTS

| | | |
|---|---|---|
| 2005/0131471 A1 | 6/2005 | Henry et al. |
| 2010/0010554 A1 | 1/2010 | Reiss |
| 2011/0098769 A1 | 4/2011 | Betzold et al. |
| 2011/0270099 A1 | 11/2011 | Ruben et al. |
| 2012/0165896 A1 | 6/2012 | Stroebel |

FOREIGN PATENT DOCUMENTS

| | | |
|---|---|---|
| CN | 101102811 A | 1/2008 |
| CN | 105579094 A | 5/2016 |
| CN | 105999549 A | 10/2016 |
| CN | 106102826 A | 11/2016 |
| CN | 106110502 A | 11/2016 |
| CN | 106951673 A | 7/2017 |
| CN | 107073267 A | 8/2017 |
| CN | 107073279 A | 8/2017 |
| CN | 107281637 A | 10/2017 |
| CN | 107281641 A | 10/2017 |
| CN | 107376120 A | 11/2017 |
| CN | 108175941 A | 6/2018 |

\* cited by examiner

METHOD AND MEDICAL DEVICE FOR IMPLEMENTING DUAL-CHAMBER PACING MODE WITHOUT VENTRICULAR PACING

TECHNICAL FIELD

Embodiments of the present invention relate to methods for control of dual-chamber pacemakers and, in particular, to a method and a medical device for implementing a dual-chamber pacing mode without ventricular pacing.

BACKGROUND

A cardiac pacemaker is an implantable therapeutic electronic device incorporating a battery-powered impulse generator for delivering an electrical impulse which is transferred via a lead to an electrode to stimulate the heart muscle to which the electrode is attached, thus controlling the heart to contract and effecting treatment of heart dysfunction caused by some cardiac arrhythmia conditions.

Dual-chamber pacemakers are capable of atrial and ventricular sensing and/or pacing. Conventional dual-chamber pacemakers are typically user-configurable to operate in dual-chamber pacing modes such as DDD, DDI, DOO, ODO, DVI and VDD. Among them, DDD pacing mode is the most commonly used and can provide atrioventricular (AV) synchronization and pacing assurance. A synchronous DDD dual-chamber mode is capable of atrial and ventricular sensing or pacing while allowing atrioventricular synchronization by ventricular pacing following an atrial event at an atrioventricular interval.

In the field of cardiac pacemakers, physiological pacing is an important topic, with minimized right ventricular pacing as one important aspect. Many pacemakers on the market such as, for example, SafeR and Dplus from the Sorin Group, Medtronic MVP and Biotronic VP Suppression, feature the capabilities of reducing right ventricular pacing. These products all follow a basic idea that right ventricular pacing can be reduced by controlling the pacemaker to operate as much as possible in an AAI or comparable mode with ventricular sensing and switch to a DDD mode only when it has to do so (e.g., when AV block occurs).

The inventors have found that the prior art is at least problematic in that the AAI mode with ventricular sensing suffers from the following deficiencies: 1) absence of VA timing (i.e., timing for sequential ventricular and atrial activation according to physiological characteristics), which is not favorable to hemodynamics; 2) lack of flexibility in handling ventricular events; and 3) non-physiological changes in timing when switching to a DDD mode. Additionally, developing a novel pacing mode is often complicated conventionally.

SUMMARY OF THE INVENTION

It is an objective of embodiments of the present invention to provide a method for implementing a dual-chamber pacing mode without ventricular pacing and a medical device. The mode enables more physiological transitioning when switching to a DDD mode, which can reduce patient discomfort and provide a sound foundation for minimizing ventricular pacing. Moreover, since this mode is based on a DDD pacing mode, dedicated mechanisms or special conditions are not required for switching between the two modes, resulting in enhanced implementation convenience, reliability and direct validatability with reduced verification workload.

The above objective is attained by a method for implementing a dual-chamber pacing mode without ventricular pacing according to embodiments of the present invention, which includes: obtaining pacing mode information configured by a user; controlling a dual-chamber pacemaker to operate in an ADD mode and detecting whether there is a need for delivering a pace; and performing a predetermined interruption process if a need for delivering a pace is detected. The predetermined interruption process includes: determining whether a chamber to be subsequently paced is a ventricle, if it is determined that the chamber to be subsequently paced is a ventricle, determining whether there is a need for delivering a real ventricular pace, and if delivery of a real ventricular pace is not needed, delivering a virtual ventricular pace VVP and resetting a first atrial escape interval, and terminating the predetermined interruption process; and returning, after the predetermined interruption process is terminated, to the step of controlling the dual-chamber pacemaker to operate in the ADD mode and detecting whether there is a need for delivering a pace.

The above objective is also attained by a medical device according to embodiments of the present invention, which includes a microprocessor and a digital/analog module connected to the microprocessor. The microprocessor is configured to control the digital/analog module to deliver pacing impulses based on heart events sensed by the digital/analog module and according to the method for implementing a dual-chamber pacing mode without ventricular pacing as defined above.

Embodiments of the present invention are advantageous over the prior art in controlling a dual-chamber pacemaker to operate in an ADD mode in which a predetermined interruption process is performed when detecting a need for delivering a pace, i.e., adding a few paths to the process flow of the conventional DDD mode. In addition, in the predetermined interruption process, if it has been determined that a chamber to be subsequently paced is a ventricle and that it is not necessary to deliver a real ventricular pace, a virtual ventricular pace VVP will be delivered simultaneously with the initiation of a new first atrial escape interval of the ADD mode. Therefore, the ADD mode is provided by utilizing the timing settings and behavior characteristics of the DDD mode. As the additions that adapt the DDD mode to the ADD mode do not change the overall functionality, operation and structure of the dual-chamber pacemaker in a significant way, the ADD mode can be provided by reusing the existing packing mode. This results in enhanced implementation convenience, reliability and direct validatability with reduced verification workload and dispenses with the need to design a brand new process flow, making the new pacing mode easy to implement, reliable and directly validatable with reduced verification workload. Moreover, switching between the ADD mode according to embodiments of the present invention and the DDD mode is more physiological than that between the DDD and AAI or enhanced AAI modes, increasing patient comfort and implementing a sound foundation for minimizing ventricular pacing.

Additionally, the predetermined interruption process may include, if it is determined that there is a need for delivering a real ventricular pace, then delivering a real ventricular pacing impulse VP, thus terminating the predetermined interruption process. In this way, the predetermined interruption process allows easy transitioning between the ADD and DDD modes.

Additionally, the predetermined interruption process may include, if it is determined that the chamber to be subsequently paced is not a ventricle, then delivering an atrial pacing impulse AP, thus terminating the predetermined interruption process. In this embodiment, when a need for delivering a pace is determined, the same predetermined interruption process is carried out, allowing the reuse of process flow.

Additionally, controlling the dual-chamber pacemaker to operate in the ADD mode and detecting there is a need for delivering a pace may particularly include: if there is no sensed heart event, then delivering an atrial pacing impulse AP, initiating an effective post-atrial pacing atrioventricular pacing interval (eff_pavi) along with a an atrial blanking period AB, a ventricular blanking period VB and an atrial refractory period ARP and if heart event is not sensed throughout the eff_pavi, determining a need for delivering a pace and performing the predetermined interruption process. In this way, the ADD mode behaves like an AAI mode.

Additionally, controlling the dual-chamber pacemaker to operate in the ADD mode and detecting there is a need for delivering a pace may further include: if a first atrial sensing signal Ar is detected within both the eff_pavi and the ARP, initiating a new AB. In this way, the ADD mode behaves like an AAI mode.

Additionally, controlling the dual-chamber pacemaker to operate in the ADD mode and detecting there is a need for delivering a pace may further include: if a second atrial sensing signal As is detected within the first atrial escape interval and outside the ARP, initiating an effective post-atrial sensing atrioventricular pacing interval (eff_savi) along with an AB and an ARP, wherein the eff_savi is the same as the eff_pavi; and if no heart event is not sensed within the eff_savi, determining a need for delivering a pace and performing the predetermined interruption process.

Additionally, controlling the dual-chamber pacemaker to operate in the ADD mode and detecting there is a need for delivering a pace may further include: if a first ventricular sensing signal Vs1 is detected within the eff_pavi and outside the VB, initiating a second atrial escape interval along with an AB, a VB, an ARP and a VRP; or if a first ventricular sensing signal Vs1 is detected within the eff_savi and outside the VB, initiating a second atrial escape interval along with an AB, a VB, an ARP and a VRP; or if no heart event is detected in the second atrial escape interval, determining, at the end of the second atrial escape interval, a need for delivering a pace and performing the predetermined interruption process.

Additionally, controlling the dual-chamber pacemaker to operate in the ADD mode and detecting there is a need for delivering a pace may further include: if a second ventricular sensing signal Vs2 is detected within the first atrial escape interval and outside the VRP, initiating a third atrial escape interval along with a VB, an ARP and a VRP; and if no heart event is detected within the third atrial escape interval, determining, at the end of the third atrial escape interval, a need for delivering a pace and performing the predetermined interruption process.

Additionally, the method may further include, subsequent to the initiation of the second atrial escape interval: if a second ventricular sensing signal Vs2 is detected within the second atrial escape interval and outside the VRP, initiating a third atrial escape interval along with an AB, a VB, an ARP and a VRP; and if no heart event is detected within the third atrial escape interval, determining, at the end of the third atrial escape interval, a need for delivering a pace and performing the predetermined interruption process; or if a ventricular sensing signal is detected within the second atrial escape interval and outside the VRP, initiating an AB, a VB, an ARP and a VRP.

BRIEF DESCRIPTION OF THE DRAWINGS

One or more embodiments will be described, by way of example, without limitation, with reference to the corresponding accompanying drawings, in which like reference numerals indicate like elements, and which do not imply any limitation on actual dimensions, unless otherwise stated.

DETAILED DESCRIPTION

The above and other objectives, features and advantages of the present invention will become more apparent from the following detailed description of various embodiments of the invention when considered in conjunction with the accompanying figures. However, it will be appreciated by those skilled in the art that while many specific details are set forth in the following embodiments in order to provide the reader with a better understanding of the invention, the subject matter of this application can be practiced without these details as well as various changes and modifications to the embodiments disclosed herein.

A first embodiment of the present invention relates to a method for implementing a dual-chamber pacing mode without ventricular pacing. The method includes: controlling a dual-chamber pacemaker to operate in an ADD mode and detecting whether there is a need for delivering a pace. If there is such a need for delivering a pace, a predetermined interruption process is carried out, which includes determining, based on a pacing mode indicated by a user input, whether a chamber to be subsequently paced is a ventricle. If so, it is determined whether there is a need for delivering a real ventricular pace. If the delivery of a real ventricular pace is not needed, then a virtual ventricular pace (VVP) is delivered, followed by the beginning of a new first atrial escape interval (AEI) of the ADD mode. At the end of the predetermined interruption process, control loops back to the step of controlling the dual-chamber pacemaker to operate in the ADD mode and detecting whether there is a need for delivering a pace. Compared with the prior art, embodiments of the present invention entail a novel ADD pacing mode. That is, a dual-chamber pacemaker can be caused to operate in a pacing mode (e.g., an ADD mode) based on a user configuration. Additionally, in terms of process flow, the ADD mode according to the present embodiment essentially operates according to the basic flow of a DDD mode, except that when it is determined that the chamber to be subsequently paced is a ventricular chamber, according to the process flow of the ADD mode, it is determined that it is not needed to deliver a real ventricular pace, a virtual ventricular pace (VVP) is delivered, followed by the beginning of a new atrial escape interval of the ADD mode. Therefore, this embodiment exhibits timing performance that is as much physiological as possible without ventricular pacing, while providing flexibility in functional extension. Implementation details of the method according to this embodiment will be described in detail below. It is to be understood that such details are provided to facilitate understanding and may not be necessary for the implementation.

Figure 1:
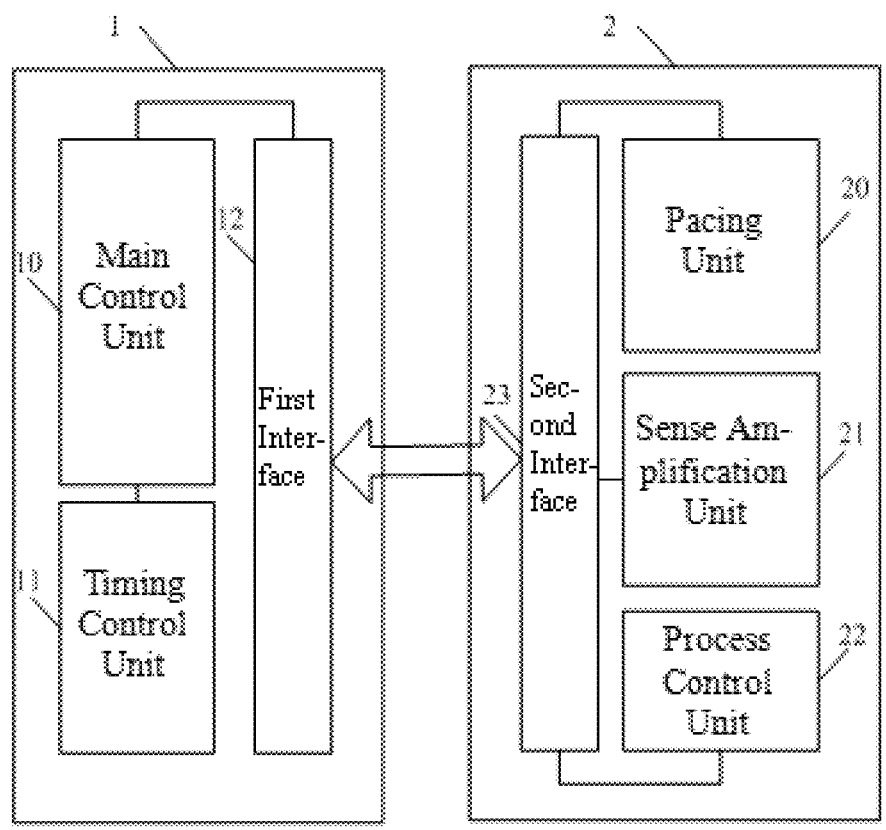
FIG. 1 schematically illustrates the structure of a dual-chamber pacemaker in which a method for implementing a dual-chamber pacing mode without ventricular pacing according to a first embodiment of the present invention can be implemented.

Reference is now made to FIG. 1, a diagram schematically illustrating the structure of a medical device (i.e., a dual-chamber pacemaker) in which a method for implementing a dual-chamber pacing mode without ventricular pacing according to a first embodiment of the present invention can be implemented. The dual-chamber pacemaker includes a microprocessor 1 and a digital/analog module 2, the microprocessor 1 is connected to the digital/analog module 2. Specifically, the microprocessor 1 includes a main control unit 10, a timing control unit 11 and a first interface 12. The main control unit 10 is configured to handle events that have occurred and are required to occur and the like, as well as for recording, statistics and the like of the events having occurred. Using the timing control unit 11, the main control unit 10 is able to perform time-related control functions such as timing, timekeeping and the like. The first interface 12 is configured for exchange of data, information or the like with the digital/analog module 2. The first interface 12 may be implemented as a regular I/O interface, a serial or parallel data transmission module or the like, and this embodiment is not limited to any particular form of the first interface. For example, the main control unit 10 may communicate with the digital/analog module 2 via an I/O interface. The digital/analog module 2 includes a pacing unit 20, a sense amplification unit 21, a process control unit 22 and a second interface 23. The second interface 23 is communicatively connected to the first interface 12 and configured for exchange of data, information and the like between the microprocessor 1 and the digital/analog module 2. The pacing unit 20 is configured to receive a pacing request from the microprocessor 1 and responsively produce an electrical impulse signal with required strength, which is then delivered externally by a respective electrode, for example, to an atrium and/or a ventricle. The sense amplification unit 21 is able to capture and identify any external true heart signal and provide it to the microprocessor 1. The process control unit 22 is configured to receive input information from a user, such as a mode switching request, configuration information and the like. The process control unit 22 provides such input information from the user to the main control unit 10 via the second interface 23 and the first interface 12, the main control unit 10 then utilizes the information to trigger a corresponding pacing mode. No matter what pacing mode the dual-chamber pacemaker is in, it is capable of both atrial and ventricular sensing. For each of the microprocessor 1, the digital/analog module 2 and other components, this embodiment is not limited to any particular form thereof. In order to provide an ADD pacing mode, a dual-chamber pacing mode without ventricular pacing, the user may configure in advance, with the process control unit 22, information about the pacing mode in which the dual-chamber pacemaker is to operate. For example, the dual-chamber pacemaker may be so configured by the process control unit as to subsequently operate in the ADD pacing mode. Additionally, the process control unit may configure an interval eff_pavi equaling an interval eff_savi and disabling functions including upper rate limit (URL) and ventricular safety pacing (VSP) so that the ADD pacing mode is more similar to an AAI pacing mode.

Figure 2:
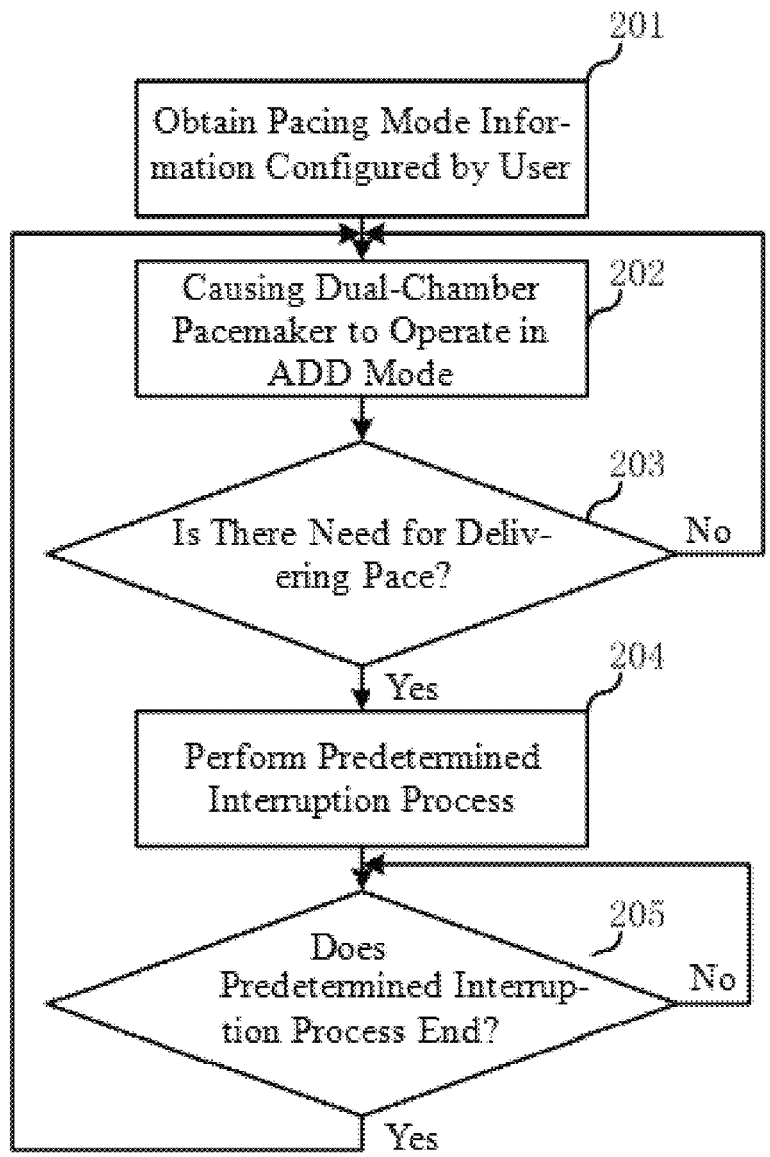
FIG. 2 is a flowchart of the method for implementing a dual-chamber pacing mode without ventricular pacing according to the first embodiment of the invention.

Referring to FIG. 2, the method for implementing a dual-chamber pacing mode without ventricular pacing according to this embodiment includes steps 201) to 205) as detailed below.

In step 201), pacing mode configuration information is obtained from the user.

The user may utilize the process control unit 22 to configure a pacing mode such as ADD, DDD or the like. The pacing mode information about the cardiac pacemaker is obtained for subsequent use. When an ADD pacing mode is selected, URL may be disabled, based on the user information from the process control unit 22. Additionally, due to the absence of ventricular pacing, the VSP function is not necessary and may also be disabled.

The following description will be made in the exemplary context of an ADD pacing mode being configured by the user.

In step 202), the dual-chamber pacemaker is caused to operate in the ADD mode.

That is to say, the dual-chamber pacemaker operates in accordance with a process flow of the ADD mode.

In step 203), it is detected whether there is a need for delivering a pace. If such a need is detected, control proceeds to step 204). Otherwise, it loops back to step 202).

In step 204), a predetermined interruption process is carried out.

Specifically, step 204) includes sub-steps 2041)-2045):

sub-step 2041): determining whether the chamber to be subsequently paced is a ventricle and proceeding to sub-step 2042) if it is a ventricle, otherwise to sub-step 2044);

sub-step 2042): determining whether the delivery of a real ventricular pace is needed and proceeding to sub-step 2045) if there is a need for a real ventricular pace, otherwise to sub-step 2043);

sub-step 2043): delivering a virtual ventricular pace (VVP), followed by the beginning of a first atrial escape interval (AEI) of the ADD mode (the first AEI is a post-ventricular AEI);

sub-step 2044): delivering an atrial pace (AP); and sub-step 2045): delivering a real ventricular pace (VP).

In step 205), it is determined whether the predetermined interruption process has been completed. Control loops back to step 202) if the determination is positive; otherwise, control remains in step 205).

It should be noted that FIG. 2 schematically shows a cyclic process flow for implementing an ADD dual-chamber pacing mode without ventricular pacing in a dual-chamber pacemaker through introducing a predetermined interruption process into a regular DDD mode. Upon the microprocessor receiving a command for quitting the ADD mode, the dual-chamber pacemaker will return to the DDD mode from said mode.

From the description given above in connection with FIG. 2, it can be seen that this embodiment provides an ADD mode, which is a DDD mode-based dual-chamber pacing mode without ventricular pacing. Therefore, the process flow of the dual-chamber pacemaker, more precisely, of the main control unit incorporates that of a DDD pacing mode. That is, the ADD mode operates in a similar way to a regular DDD pacing mode in response to an atrial or ventricular sensing event, but it adds an additional option on the basis of the DDD mode when the pacing needs to be delivered, that is for delivering either a real ventricular pacing (VP) impulse or a virtual ventricular pace (VVP) by the predetermined interruption process.

The method for implementing a dual-chamber pacing mode without ventricular pacing according to this embodiment will be described in greater detail below with reference to FIGS. 4 to 10, which show functional timing diagrams of the ADD pacing mode. In other words, FIGS. 4 to 10 illustrate various functions of the ADD pacing mode according to this embodiment.

In this embodiment, in response to the reception of information about the ADD pacing mode from the user, the dual-chamber pacemaker will operate in the ADD mode and delivers, when there is no sensed heart event, an atrial pacing impulse AP, indicated at Ap① in FIGS. 4 to 10, is delivered, followed by the initiation of an effective post-atrial pacing atrioventricular pacing interval (eff_pavi), an atrial blanking (AB) period, ventricular blanking (VB) period and atrial refractory period (ARP). The interval and periods are the same as those in a regular DDD mode and will not be further detailed herein. Possible cases that may occur following the delivery of Ap①, as well as respective processes for handling such cases, will be described in detail below.

Figure 4:
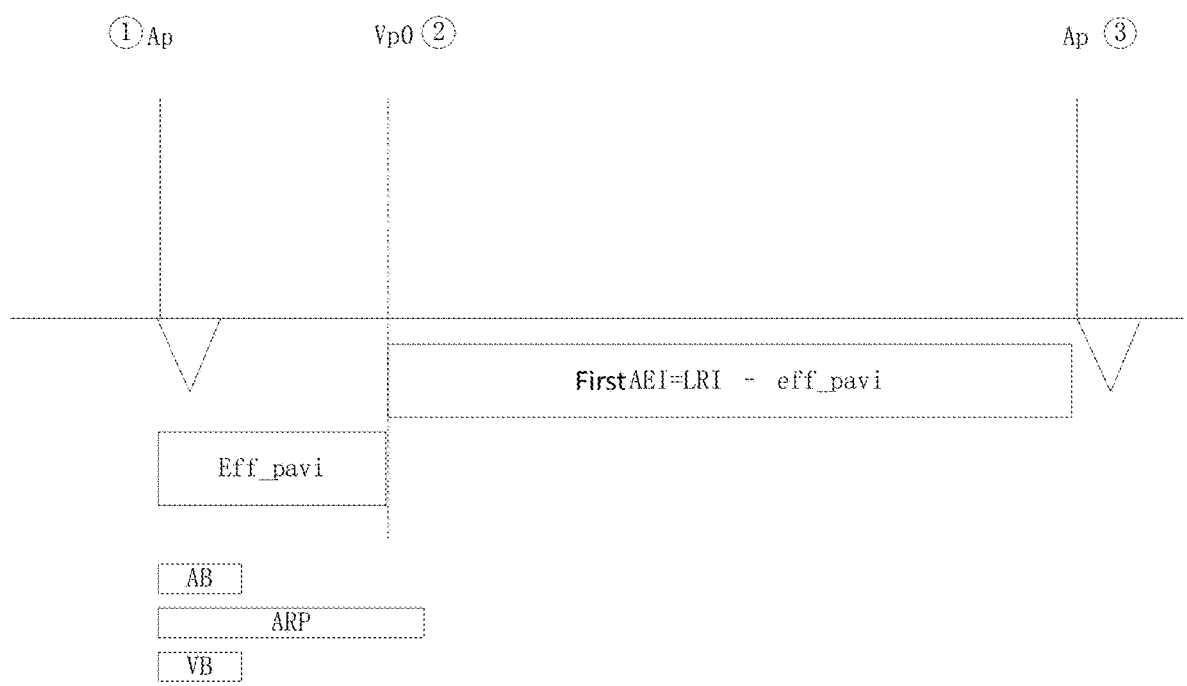
FIGS. 4-10 depict functional timing diagrams of the method for implementing a dual-chamber pacing mode without ventricular pacing according to the first embodiment of the invention.

Case 1: If no heart event is sensed throughout the interval eff_pavi, then a need is determined to deliver a pace. At this point, the predetermined interruption process, i.e., step 204), is carried out. Specifically, as shown in FIG. 4, when the dual-chamber pacemaker does not detect any heart event, an atrial pace Ap① is delivered, marking the simultaneous beginning of the interval eff_pavi, the AB and VB periods and the ARP. If no heart event is detected within the whole interval eff_pavi, a virtual ventricular pacing Vp0②(which does not actually pace the heart) is delivered at the end of eff_pavi, and the time when Vp0② is generated is recorded, followed by a first atrial escape interval (AEI) beginning at Vp0②. The first AEI is equal to a lower rate interval (LRI) minus eff_pavi, and there is no any other interval initiated simultaneously with the first AEI. If there is no sensing event occurring throughout the first AEI, another atrial pace Ap③ is delivered at the end of the first AEI. In this case, the ADD mode behaves like an AAI mode. It should be noted that each set of circled numbers in FIGS. 4 to 10 implies an order in which the marked pace delivery and sensing events occur.

Figure 5:
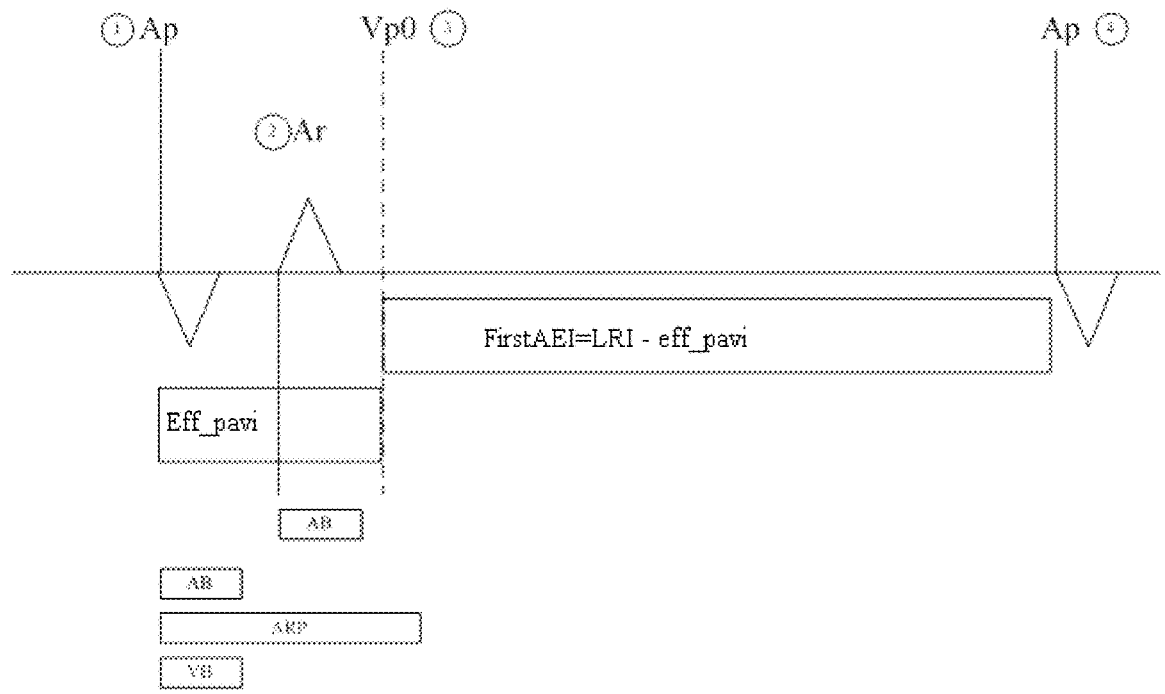

Case 2: After the delivery of the atrial pace Ap①, if a first atrial sensing signal Ar is detected both in the intervals eff_pavi and ARP, then another AB period of the ADD mode is initiated. Specifically, referring to FIG. 5, if an atrial sensing signal Ar② (i.e., the first atrial sensing signal) is detected within both the intervals eff_pavi and ARP, it is determined that an atrial sensing event has occurred in the atrial refractory period. At this point, another AB period, i.e., a new AB period, is initiated at the detection time of Ar②, and a virtual ventricular pacing Vp0③(which does not actually pace the heart) is delivered at the end of the interval eff_pavi, and a first AEI (=LRI-eff_pavi) beginning at Vp0③ is initiated without any other interval starting at the same time. If there is no sensing event occurring throughout the first AEI, another atrial pace Ap④ is delivered at the end of the first AEI. It should be noted that no matter the atrial sensing signal is detected within an ARP that is initiated in response to an atrial or ventricular event, it behaves like Ar② in FIG. 5. In the case as shown in FIG. 5, the ADD mode behaves like an AAI mode.

Figure 6:
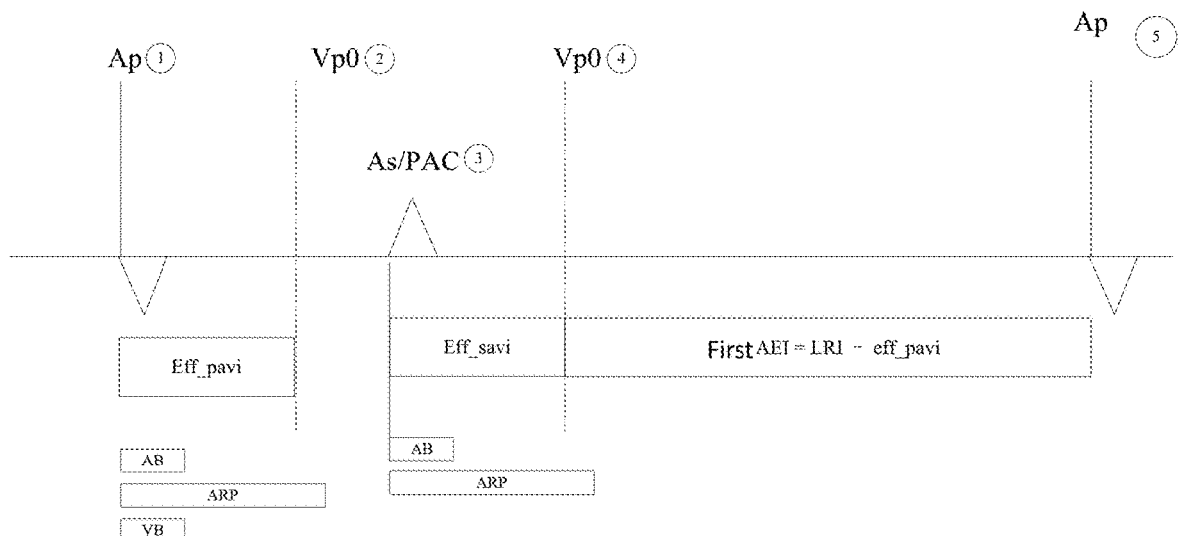

Case 3: After the delivery of the atrial pace Ap①, there is no sensing event detected within interval eff_pavi, then a virtual ventricular pacing Vp0② is delivered at the end of the interval eff_pavi, resulting in the initiation of a first AEI beginning at Vp0②(similar to that of FIG. 4). If a second atrial sensing signal As is detected within the first AEI and outside the ARP, then an effective post-atrial sensing atrioventricular pacing interval (eff_savi) is initiated together with a new AB period and a new ARP of the ADD mode. In order for the ADD mode to behave more like an AAI mode, eff_savi may be configured to be equivalent to eff_pavi. If no heart event is sensed throughout the interval eff_savi, then a predetermined interruption process is carried out. Specifically, as shown in FIG. 6, if an atrial sensing signal As③ is detected within the first AEI and outside the ARP beginning at Ap①, it is regarded as a second atrial sensing signal. Since As③ is an atrial sensing event occurring outside the atrial refractory period, it is determined that it is very likely associated with a premature atrial contraction (PAC) event. The signal As③ is followed by an interval eff_savi (i.e., the effective post-atrial sensing atrioventricular pacing interval), which is initiated simultaneously with a new AB period and a new ARP, wherein eff_savi=eff_pavi. If no sensing event occurs within the interval eff_savi, a virtual ventricular pacing Vp0④(which does not actually pace the heart) is delivered at the end of the interval eff_savi. The part of this process flow following Vp0④ is similar to that in FIG. 5 and will not be described again for brevity. In the case of FIG. 6, the ADD mode behaves like an AAI mode.

Figure 7:
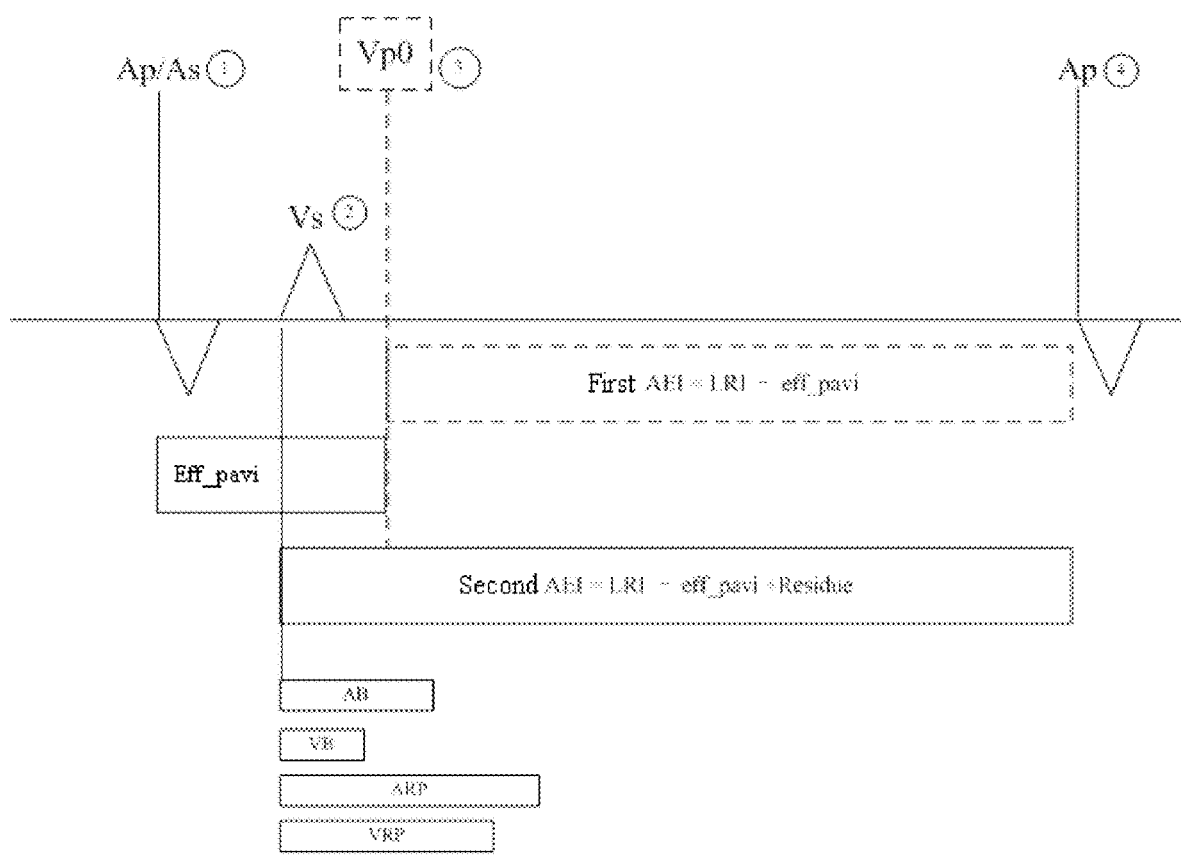

Case 4: Following Ap① or As①, eff_pavi or eff_savi is initiated simultaneously with an AB period, a VB period and an ARP (the AB and VB periods and ARP each beginning at Ap/As① are omitted in the figure. Additionally, as eff_pavi is configured to be equal to eff_savi, it is also omitted). If a first ventricular sensing signal Vs1 is detected within the interval eff_pavi and outside the VB period, a second atrial escape interval (AEI) of the ADD mode is initiated along with an AB period, a VB period, an ARP and a ventricular refractory period (VRP). Alternatively, if a first ventricular sensing signal Vs1 is detected within the interval eff_savi and outside the VB period, then a second atrial escape interval (AEI) of the ADD mode is initiated along with an AB period, a VB period, an ARP and a VRP. If no heart event is detected within the second AEI, then a predetermined interruption process is performed at the end of the second AEI. Specifically, with reference to FIG. 7, a ventricular sensing signal Vs② (i.e., the first ventricular sensing signal Vs1) is detected within the interval eff_pavi or eff_savi and outside the VB period (not shown). As Vs® is identified as a ventricular sensing signal occurring outside a refractory period, a second AEI is initiated (where the second AEI=LRI-eff_pavi+residue; residue=eff_pavi-av_intvl; and av_intvl=Ap/As①-to-Vs② interval) along with an AB period, a VB period and an ARP, and no virtual ventricular pacing Vp0③ is delivered. If no sensing signal is detected through the second AEI, an atrial pacing signal Ap④ is delivered at the end of second AEI. Due to absence of ventricular pacing, the ADD mode does not provide a ventricular safety pacing (VSP) function. In the case of FIG. 7, the ADD mode behaves like an AAI mode.

Figure 8:
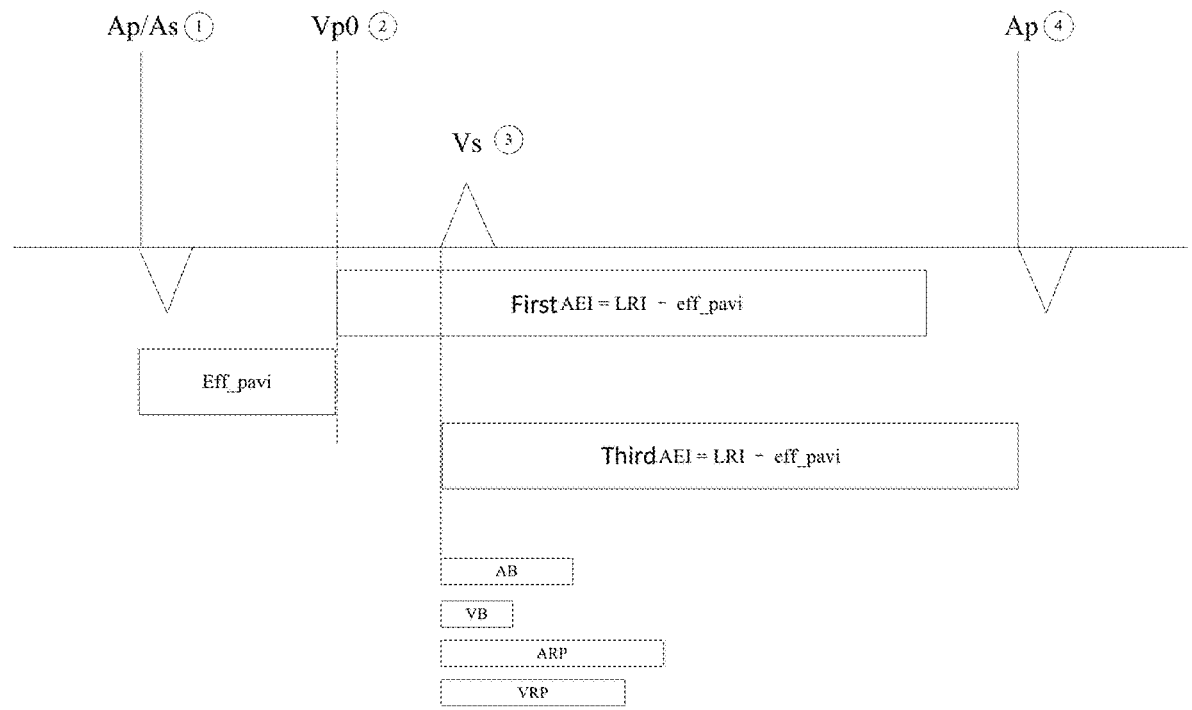

Case 5: Following Ap① or at As①, eff_pavi or eff_savi is initiated. If a second ventricular sensing signal Vs2 is detected within a first AEI, a third atrial escape interval (AEI) of the ADD mode is initiated along with an AB period, a VB period, an ARP and a VRP. If no heart event is sensed in the third AEI, a predetermined interruption process is performed at the end of the third AEI. Specifically, referring to FIG. 8, if a ventricular sensing signal (i.e., the second ventricular sensing signal Vs2) is detected in the first AEI, the signal Vs2 will be identified as a signal Vs③. Accordingly, a third AEI, which is equal to LRI minus eff_pavi, is initiated along with an AB period, a VB period, an ARP and a VRP. If no sensing signal is detected throughout the third AEI, an atrial pacing signal Ap④ is delivered at the end of the third AEI. As shown in FIG. 8, compared to the AAI or enhanced AAI mode, the ADD mode additionally provides VA timing, resulting in improved hemodynamic performance.

Figure 9:
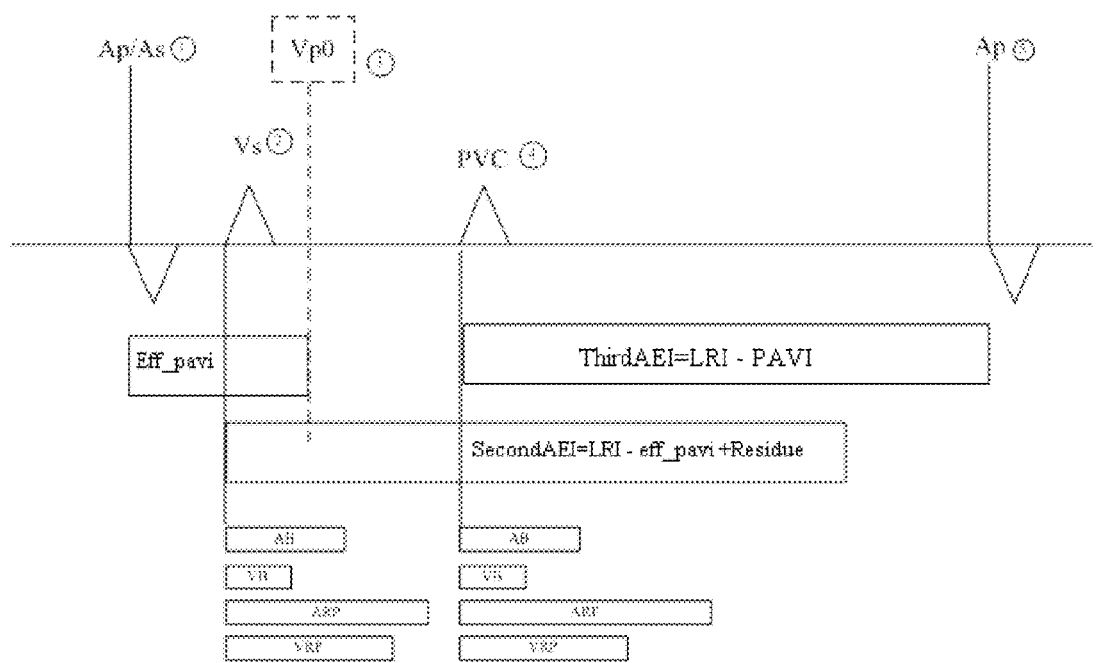

Case 6: Following Ap①  or at As①, eff_pavi or eff_savi is initiated along with an AB period, a VB period and an ARP. If a first ventricular sensing signal Vs1 (Vs②) is detected within eff_pavi or eff_savi and outside the VB period, a second atrial escape interval (AEI) of the ADD mode is initiated along with an AB period, a VB period, an ARP and a VRP. If a second ventricular sensing signal Vs2 is detected within the second AEI and outside the VRP, a third AEI is initiated along with an AB period, a VB period, an ARP and a VRP. If no heart event is sensed throughout the third AEI, then a predetermined interruption process is performed at the end of the third AEI. Specifically, with reference to FIG. 9, a ventricular sensing signal (i.e., the second ventricular sensing signal Vs2) is detected in the second AEI beginning at Vs② (without Vp0③ being delivered any longer) and identified as Vs PVC④ (i.e., a ventricular sensing signal occurring outside of a refractory period and indicating a premature ventricular contraction). Responsively, a third AEI (=LRI−eff_pavi) is initiated along with an AB period, a VB period, an ARP and a VRP. In this case, the VRP is longer. If no sensing signal is detected within the third AEI, then an atrial pacing signal Ap⑤ is delivered at the end of the third AEI. As shown in FIG. 9, VA timing will be provided upon the occurrence of ventricular tachycardia or more PVCs, temporarily inhibiting atrial pace (AP) delivery and reducing unphysiological short depolarization of the atrial and ventricular chambers.

Case 7: Following Ap① or at As①, eff_pavi or eff_savi is initiated along with an AB period, a VB period and an ARP. If a first ventricular sensing signal Vs1 (Vs②) is detected within eff_pavi or interval eff_savi and outside the VB period, a second atrial escape interval (AEI) of the DDD mode is initiated along with an AB period, a VB period, an ARP and a VRP. If a ventricular sensing signal is detected within both the second AEI and the VRP, then an AB period, a VB period, an ARP and a VRP are initiated. Specifically, referring to FIG. 10, on the basis of FIG. 7, a ventricular sensing signal is detected in both the second AEI beginning at Vs② (without Vp0③ being delivered any longer) and the VRP and is identified as Vr PVC④ (i.e., a ventricular sensing signal occurring outside of a refractory period and indicating a premature ventricular contraction). Responsively, an AB period, a VB period, an ARP and a VRP are initiated. In this case, the ARP is longer. Subsequently, an atrial pacing signal Ap⑤ is delivered at the end of the second AEI.

Except for the above-described ADD functions, all the other functions of this embodiment are equivalent to those of the conventional DDD mode.

From the above description, it can be seen that the ADD mode according to this embodiment is essentially similar to the conventional DDD mode, except for a few additions to operation of the latter, which, however, do not change the overall functionality, operation and structure of the DDD mode in a significant way. Therefore, the novel ADD mode according to this embodiment can be provided by reusing the existing (DDD pacing) mode. This dispenses with the need to design a brand new process flow, making the new pacing mode easy to implement, reliable and directly validatable with reduced verification workload. Moreover, since the ADD mode is provided by reusing the DDD mode, there is a certain degree of similarity between the two modes, which allows more natural switching and more physiological transitioning between the DDD and ADD modes, resulting in improved patient comfort and implementing a sound foundation for minimizing ventricular pacing. Further, the switching between the DDD and ADD modes is better than that between the DDD and AAI or enhanced AAI modes.

The boundaries of the steps in the method as defined above are merely illustrative, and in practice, it is possible to combine multiple of the steps into one or divide one of the steps into several, without departing from the scope of the present invention, as long as such combination or division does not lead to logic changes. Introduction of insignificant modifications or design changes to any algorithm or process flow disclosed herein, which do not alter the essence of the algorithm or process, are also intended to be embraced in the scope of the invention.

A second embodiment of the present invention relates to a medical device, which, with continued reference to FIG. 1, includes a microprocessor and a digital/analog module connected to the microprocessor. The medical device of this embodiment has the same structure as that of the dual-chamber pacemaker according to the first embodiment and need not be described any further.

Functions of a dual-chamber pacing mode without ventricular pacing (novel ADD mode) provided by the medical device according to this embodiment will be described in detail below with continued reference to the functional timing diagrams of the ADD mode shown in FIGS. 4 to 10.

Figure 3:
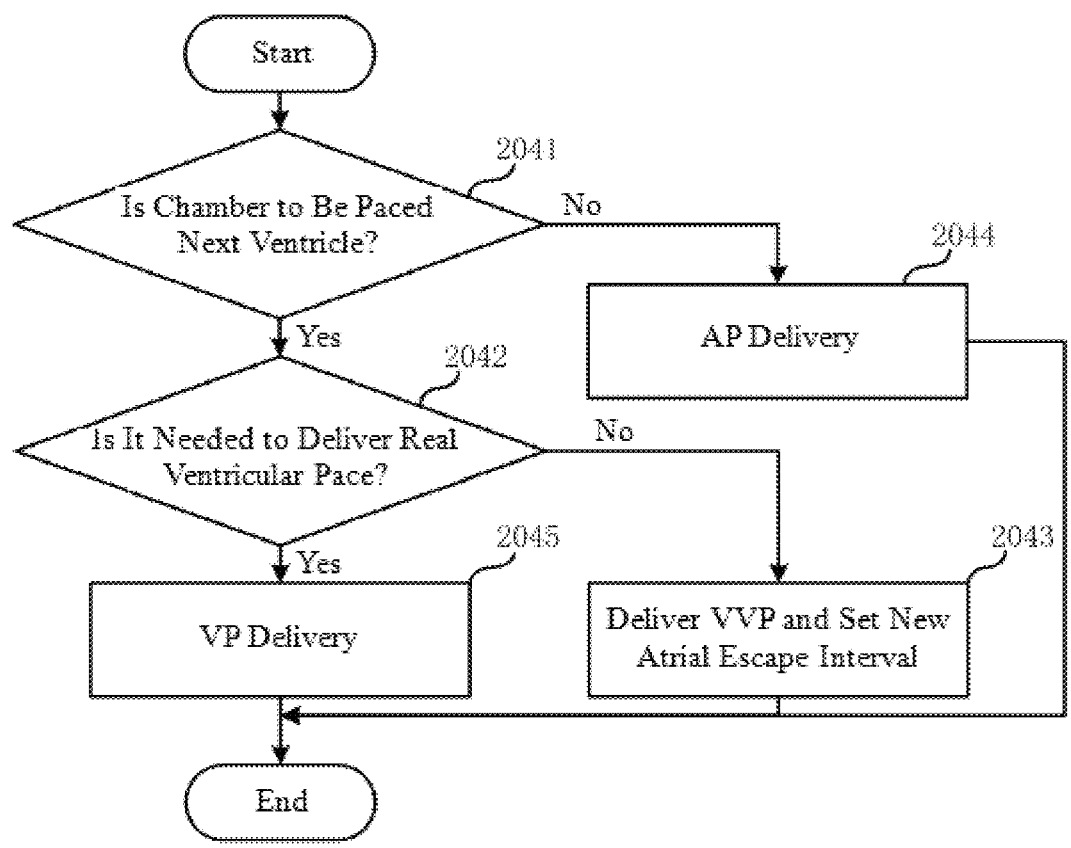
FIG. 3 is a flowchart of a predetermined interruption process in the method for implementing a dual-chamber pacing mode without ventricular pacing of FIG. 2.

Referring to FIGS. 4 and 1, in this embodiment, in response to an atrial pace Ap① delivered by the digital/analog module 2, the microprocessor 1 operates in the DDD mode in which the main control unit 10 causes the timing control unit 11 to initiate a AB period, a VB period, an ARP and an interval eff_pavi, where ARP>eff_pavi. Upon expiry of the interval eff_pavi initiated and maintained by the timing control unit 11, the main control unit 10 performs the predetermined interruption process of FIG. 3 in which the main control unit 10 determines whether the chamber being currently paced is a ventricle. In this embodiment, the chamber being currently paced is, for example, ventricular, and the main control unit 10 determined, based on pacing mode information obtained from the user by the process control unit, that ventricular pacing is not needed in the current mode. Thus, the main control unit 10 delivers a pace as a VVP event (i.e., Vp②) and calculates a first AEI beginning at Vp ② according to the formula: the first AEI=LRI−eff_pavi. At the same time, it instructs the timing control unit to set the first AEI, and the main control unit 10 again performs the predetermined interruption process shown in FIG. 3 upon expiry of the first AEI maintained by the timing control unit 11. At this point, the main control unit 10 determines that the chamber being currently paced is atrial and the main control unit 10 delivers a pacing request signal to the pacing unit 20, the pacing unit 20 then produces a signal Ap③ with a level of strength as indicated by the pacing request signal and delivers it to the target atrium. The digital/analog module 2 then performs the part of the process flow subsequent to the delivery of the atrial pace Ap ③.

Referring to FIGS. 5 and 1, before the interval eff_pavi maintained by the timing control unit 11 expires, the sense amplification unit 21 captures an atrial signal ② and informs the microprocessor 1 thereof. When the main control unit 10 determines that the ARP currently maintained by the timing control unit 11 has not expired yet, it records that as an Ar event (Ar②) and starts another AB period. When the sense amplification unit 21 captures any external atrial signal during the ARP and informs the microprocessor 1 thereof, such an event will be recorded as an Ar event, concurrently with the initiation of a new AB period. Upon expiry of the interval eff_pavi maintained by the timing control unit 11, the main control unit 10 records this as a virtual ventricular pacing (VVP) event (Vp0③) and performs a corresponding handling process.

Referring to FIGS. 6 and 1, the sense amplification unit 21 captures an external atrial signal ③ after the ARP maintained by the timing control unit 11 has expired and informs the microprocessor 1 thereof, and the main control unit 10 records this as an As event (As③) and initiates an AB period, an ARP and an interval eff_savi, where eff_savi=eff_pavi and ARP>eff_pavi. Upon expiry of the interval eff_savi maintained by the timing control unit 11, the main control unit 10 records this as a virtual ventricular pacing (VVP) event Vp0④ and performs a corresponding handling process.

Referring to FIGS. 7 and 1, the sense amplification unit 21 captures an external ventricular signal CD before expiry of the interval eff_pavi maintained by the timing control unit 11 and informs the microprocessor 1 thereof, and the main control unit 10 records it as a Vs event (Vs②) and calculates a second AEI according to the formula: the second AEI=LRI−eff_pavi+residue, where residue=eff_pavi−(Ap/As①-to-Vs② interval). At the same time, it instructs the timing control unit 11 to initiate an AB period, a VB period, an ARP, a VRP and the second AEI, each beginning at the current instant. Upon expiry of the second AEI maintained by the timing control unit 11, the main control unit 10 transmits a pacing request signal to the pacing unit 20, the pacing unit 20 then produces a signal Ap④ with a level of strength as requested and delivers it to the target atrium. In this case, no VVP (Vp0③) event is recorded and handled.

Referring to FIGS. 8 and 1, the sense amplification unit 21 captures an external ventricular signal ③ before the VRP maintained by the timing control unit 11 expires and informs the microprocessor 1 thereof, and the main control unit 10 records it as a Vs event (Vs ③) and calculates a third AEI according to the formula: the third AEI=LRI−eff_pavi. At the same time, it causes the timing control unit 11 to initiate an AB period, a VB period, an ARP, a VRP and the third AEI, each beginning at the current instant. Upon expiry of the third AEI maintained by the timing control unit 11, the main control unit 10 transmits a pacing request signal to the pacing unit 20, the pacing unit 20 then produces a signal Ap④ with strength as requested and delivers it to the target atrium.

Referring to FIGS. 9 and 1, subsequent to the occurrence of a ventricular sensing event Vs②, the sense amplification unit 21 captures another external ventricular signal ④ before the VRP maintained by the timing control unit 11 expires and informs the microprocessor 1 thereof, and the main control unit 10 records the event as both a Vs event and a PVC event (PVC④) and calculates a third AEI according to the formula: the third AEI=LRI−eff_pavi. At the same time, it instructs the timing control unit 11 to initiate an AB period, a VB period, an ARP, a VRP and the third AEI, each beginning at the current instant. The VRP beginning at PVC④ is longer than that at the instant of the ventricular sensing signal Vs②. Upon expiry of the third AEI maintained by the timing control unit 11, the main control unit 10 transmits a pacing request signal to the pacing unit 20, the pacing unit 20 then produces a signal Ap⑤ with strength as requested and delivers it to the target atrium. In this case, the main control unit 10 does not record or handle any VVP (Vp0③) event.

Figure 10:
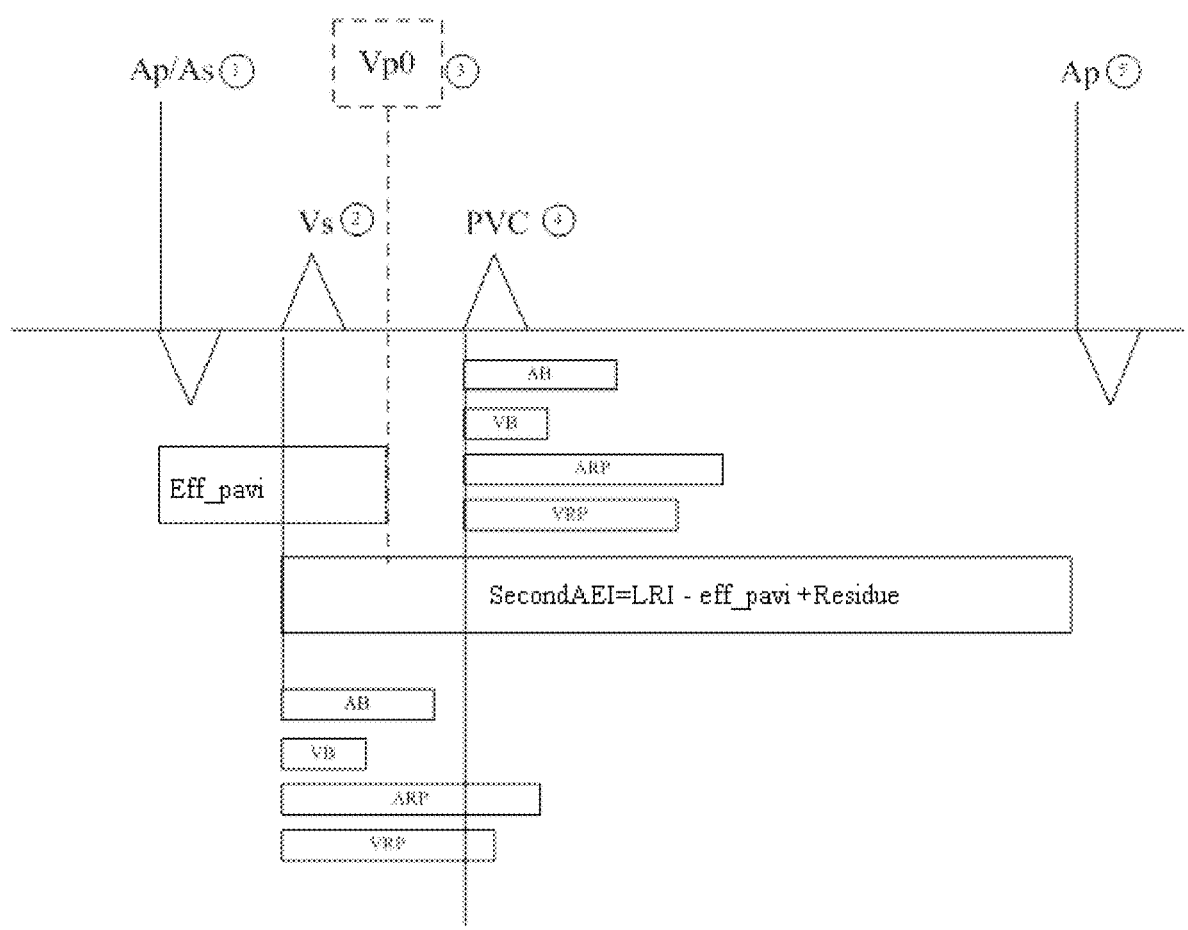

Referring to FIGS. 10 and 1, subsequent to the occurrence of a ventricular sensing event Vs②, the sense amplification unit 21 captures another external ventricular signal ④ before the VRP maintained by the timing control unit 11 expires and informs the microprocessor 1 thereof, and the main control unit 10 records that event as both a Vr event and a PVC event (PVC④) and instructs the timing control unit 11 to initiate an AB period, a VB period, an ARP and a VRP, each beginning at the current instant. The VRP beginning at PVC④ is longer than that at the instant of the ventricular sensing signal Vs ②. Upon expiry of the second AEI maintained by the timing control unit 11, the main control unit 10 transmits a pacing request signal to the pacing unit 20, the pacing unit 20 then produces a signal Ap⑤ with strength as requested and delivers it to the target atrium. In this case, no VVP (Vp0③) event is recorded and handled.

Compared with the prior art, the ADD mode according to this embodiment is essentially similar to the DDD mode, except for a few additions to the process flow of the latter, which, however, do not change the overall flow in a significant way. Therefore, the ADD mode is provided by reusing that process flow based on a determination on the current operating mode. This dispenses with the need to design a brand new process flow, making the new pacing mode easy to implement, reliable and directly validatable with reduced verification workload. Additionally, switching between the DDD and ADD modes is better than that between the DDD and AAI or enhanced AAI modes and allows more physiological transitioning, resulting in improved patient comfort and implementing a sound foundation for minimizing ventricular pacing.

As can be readily seen, this device embodiment corresponds to the above first embodiment and can be implemented in combination therewith. As the technical details mentioned in the first embodiment are equally applicable to this embodiment, they are not described in detail here for the sake of brevity. Correspondingly, the technical details mentioned in this embodiment can also be similarly applied to the first embodiment.

Notably, the various modules described in connection with the foregoing embodiments are all logic modules. In practical applications, a logical module can be implemented by either a monolithic physical module or part thereof or by a combination of multiple physical modules. In addition, components that are not closely related to the problem sought to be solved by the disclosed embodiments are not mentioned herein in order to emphasize the inventiveness of the present invention, but this does not preclude the presence of these components in the embodiments.

Those of ordinary skill in the art will appreciate that the above embodiments are provided as specific examples for practicing the present invention and may be modified in the form and details without departing from the spirit and scope thereof.

What is claimed is:

1. A method for implementing a dual-chamber pacing mode, the method comprising:
   step 1) obtaining pacing mode information configured by a user;
   step 2) controlling a dual-chamber pacemaker to operate in an ADD mode;
   step 3) detecting whether there is a need for delivering a pace, if a need for delivering a pace is detected, proceeding to step 4), otherwise, looping back to step 2);

step 4) performing a predetermined interruption process; and step 5), it is determined whether the predetermined interruption process has been completed, looping back to step 2) if the determination is positive, otherwise, remaining in step 5), wherein the predetermined interruption process comprises:

sub-step a) determining whether a chamber to be subsequently paced is a ventricle and proceeding to sub-step b) if it is determined that the chamber to be subsequently paced is a ventricle, otherwise to sub-step d);

sub-step b) determining whether there is a need for delivering a real ventricular pace and proceeding to sub-step e) if there is a need for a real ventricular pace, otherwise to sub-step c);

sub-step c) delivering a virtual ventricular pace VVP and resetting a first atrial escape interval;

sub-step d) delivering an atrial pacing impulse AP;

sub-step e) delivering a real ventricular pacing impulse VP.

2. The method for implementing a dual-chamber pacing mode of claim 1, wherein controlling the dual-chamber pacemaker to operate in an ADD mode and detecting whether there is a need for delivering a pace comprises:

if no heart event is sensed, then delivering an atrial pacing impulse AP, initiating an effective post-atrial pacing atrioventricular pacing interval eff_pavi, and also initiating an atrial blanking period AB, a ventricular blanking period VB and an atrial refractory period ARP, and if no heart event is sensed within the eff_pavi, determining a need for delivering a pace and performing the predetermined interruption process.

3. The method for implementing a dual-chamber pacing mode of claim 2, wherein controlling the dual-chamber pacemaker to operate in an ADD mode and detecting whether there is a need for delivering a pace further comprises:

if a first atrial sensing signal Ar is detected within the eff_pavi and the Ar is within the ARP, resetting the AB.

4. The method for implementing a dual-chamber pacing mode of claim 2, wherein controlling the dual-chamber pacemaker to operate in an ADD mode and detecting whether there is a need for delivering a pace further comprises:

if a second atrial sensing signal As is detected within the first atrial escape interval and the As is outside the ARP, initiating an effective post-atrial sensing atrioventricular pacing interval eff_savi and resetting the AB and the ARP, wherein the eff_savi is configured to be equal to the eff_pavi; and if no heart event is sensed within the eff_savi, determining a need for delivering a pace and performing the predetermined interruption process.

5. The method for implementing a dual-chamber pacing mode of claim 4, wherein controlling the dual-chamber pacemaker to operate in an ADD mode and detecting whether there is a need for delivering a pace further comprises:

if a first ventricular sensing signal Vs1 is detected within the eff_pavi and outside the VB, initiating a second atrial escape interval and also initiating an AB, a VB, an ARP and a VRP; or if a first ventricular sensing signal Vs1 is detected within the eff_savi and outside the VB, initiating a second atrial escape interval and also initiating an AB, a VB, an ARP and a VRP; or if no heart event is detected in the second atrial escape interval, determining, at an end of the second atrial escape interval, a need for delivering a pace and performing the predetermined interruption process.

6. The method for implementing a dual-chamber pacing mode of claim 5, wherein controlling the dual-chamber pacemaker to operate in an ADD mode and detecting whether there is a need for delivering a pace further comprises:

if a second ventricular sensing signal Vs2 is detected within the first atrial escape interval and outside the VRP, initiating a third atrial escape interval and also initiating a VB, an ARP and a VRP; and if no heart event is detected within the third atrial escape interval, determining, at an end of the third atrial escape interval, a need for delivering a pace and performing the predetermined interruption process.

7. The method for implementing a dual-chamber pacing mode of claim 5, further comprising, subsequent to the initiation of the second atrial escape interval:

if a second ventricular sensing signal Vs2 is detected within the second atrial escape interval and outside the VRP, initiating a third atrial escape interval and also initiating an AB, a VB, an ARP and a VRP; and if no heart event is detected within the third atrial escape interval, determining, at an end of the third atrial escape interval, a need for delivering a pace and performing the predetermined interruption process; or if a ventricular sensing signal is detected within the second atrial escape interval and outside the VRP, initiating an AB, a VB, an ARP and a VRP.

8. A medical device, comprising a microprocessor and a digital/analog module connected to the microprocessor, the microprocessor configured to control the digital/analog module to deliver pacing impulses based on heart events sensed by the digital/analog module and according to the method for implementing a dual-chamber pacing mode as defined in claim 1.

* * * * *